(12) United States Patent
Osborne

(10) Patent No.: US 6,620,435 B1
(45) Date of Patent: *Sep. 16, 2003

(54) COMPOSITIONS FOR TOPICAL APPLICATION OF THERAPEUTIC AGENTS

(75) Inventor: David W. Osborne, The Woodlands, TX (US)

(73) Assignee: ViroTex Corporation, The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/236,909

(22) Filed: Jan. 25, 1999

Related U.S. Application Data

(63) Continuation of application No. 08/712,454, filed on Sep. 11, 1996, now Pat. No. 5,863,560.

(51) Int. Cl.[7] .......................... A61K 9/10; A61K 47/32; A61K 47/38
(52) U.S. Cl. .................. 424/487; 424/484; 424/488; 514/944
(58) Field of Search ............................. 424/484–488; 514/859, 944

(56) References Cited

U.S. PATENT DOCUMENTS

| | | | |
|---|---|---|---|
| 3,867,533 A | * | 2/1975 | Schmolka |
| 4,507,287 A | * | 3/1985 | Dixon |
| 4,731,359 A | | 3/1988 | Swarbrick |
| 4,853,439 A | | 8/1989 | Barabas |
| 5,180,576 A | * | 1/1993 | Winston et al. |
| 5,585,379 A | * | 12/1996 | Sintov et al. |
| 5,643,584 A | | 7/1997 | Farng et al. |
| 5,705,194 A | | 1/1998 | Wong et al. |
| 5,863,560 A | * | 1/1999 | Osborne |

FOREIGN PATENT DOCUMENTS

| | | |
|---|---|---|
| EP | 0 679 390 A3 | 11/1995 |
| GB | 2 260 080 A | 4/1993 |

OTHER PUBLICATIONS

Freeman, D.J. et al., "Failure of topical acyclovir in ointment to penetrate human skin" *Antimicrobial agents and chemotherapy* 29(5):730–732 (May 1986).

Hostýnek, J.J. et al., "Human skin penetration by metal compounds" in *Dermal Absorption and Toxicity Assessment*, Chapter 25, edited by Roberts, M.S. and Walters, K.A., published by Marcel Dekker, Inc., pp. 647–668 (1998).

* cited by examiner

*Primary Examiner*—Edward J. Webman
(74) *Attorney, Agent, or Firm*—Morrison & Foerster LLP

(57) ABSTRACT

The present invention generally relates to pharmaceutical compositions that enable control of drug, delivery properties and the development of optimal drug delivery strategies customized for particular drugs and particular diseases. The composition includes a dissolved pharmaceutical that has the capacity to permeate the stratum corneum layer of the epidermis and become available systemically, and a pharmaceutical in a microparticulate state that does not readily cross the stratum corneum of the epidermis. The dissolved and microparticulate pharmaceuticals may be the same or different pharmaceuticals. Methods for the preparation and use of the compositions are also provided. In a preferred embodiment, the invention finds particular use in a formulation for the topical application of dapsone for the treatment of acne. In another preferred embodiment, the invention finds particular use for the treatment of herpes lesions.

15 Claims, No Drawings

COMPOSITIONS FOR TOPICAL APPLICATION OF THERAPEUTIC AGENTS

This application is a continuation of Ser. No. 08/712,454, filed Sep. 11, 1996, now U.S. Pat. No. 5,863,560.

FIELD OF THE INVENTION

The present invention relates to novel dermatological compositions that exhibit readily optimized solubility and systemic drug delivery properties for applying drugs and therapeutic agents to the skin of humans and animals and methods for their preparation and use.

BACKGROUND OF THE INVENTION

While the skin has long been considered the preferred route of administration for cosmetic applications and dermatological therapies, the introduction of transdermal nitroglycerin patches initiated use of the skin as a route for administering systemic drug therapy. Three types of known product applications which employ the barrier properties of the skin for drug delivery include cosmetic, topical, and transdermal applications. The optimal delivery strategy for administering pharmaceuticals via the skin varies among individual pharmaceuticals and among different disease states.

Cosmetic applications are limited to negligible drug penetration past the stratum corneum. Thus, any carrier that minimizes penetration or that aids excipient retention within or onto the stratum corneum would be of tremendous advantage. For transdermal applications, steady state drug delivery is preferred. Steady state delivery requires the use of rate-controlling membranes that slow systemic breakthrough of highly permeable drugs such as nitroglycerin. This type of control can be achieved by using matrix type patches that modify delivery rates by using polymer adhesives and solvents. For topical delivery, minimal systemic breakthrough is always preferred. In order to adequately dose the viable epidermis and dermis, however, large amounts of drug must cross the intact skin barrier, i.e. the stratum corneum, or the lesional delivery barrier, i.e. scab, plaque, etc.

Some dermatological conditions, such as acne, require multiple delivery strategies because they have multiple delivery requirements. Acne is chronic pilosebaceous unit inflammation associated with the face and trunk usually occurring in adolescence due to complex interactions of androgens and bacteria. For the adolescent, circulating androgen results in significantly increased sebum production. The sebaceous glands dramatically enlarge and excrete more sebum than the immature pilosebaceous canals can accommodate. Simultaneously, anaerobic bacteria (*Propionibacterium acnes*) that feed upon the sebum, converting triglycerides to fatty acids, dramatically increase in number due to an increase in volume of the nutrition source. The increase in constricted immature ducts and bacterial waste products results in plugged follicles and typical acne inflammation. Acne severity for a particular anatomical location parallels the number of sebaceous glands per unit of skin.

Acne, which is often treated with antibiotics, is one condition where a highly specialized topical drug delivery is needed. Ideally, a topical antimicrobial would be primarily delivered into the pilosebaceous unit, with only minimal active crossing of the skin barrier. Intact stratum corneum lines the upper third of the pilosebaceous unit, and it is into this upper third of the hair follicle that the sebaceous duct secretes sebum. Thus, a need exists for an acne treatment that maximizes antimicrobial drug levels in the upper third of the pilosebaceous unit.

Additionally, when an anti-inflammatory agent is used to treat acne, it is important to increase the level of drug that will cross the intact stratum corneum lining the upper third of the pilosebaceous unit. By definition, inflammation is the response of the viable epidermis to irritants and sensitizers. In order to reduce the amount of inflammation, the active pharmaceutical must penetrate past the stratum corneum and interfere with the cascade of inflammatory events. Ideally, delivery of an anti-inflammatory for acne requires that steady-state levels be sustained. To date, the ideal delivery system that provides antimicrobial agents above the stratum corneum while providing anti-inflammatory agents below the stratum corneum has not been implemented.

Other dermatological conditions, such as herpes lesions, require multiple delivery strategies because the barrier properties of the lesion dramatically change in the course of the disease. Starting with the prodrome and progressing through the formation of vesicles, the lesion has an intact stratum corneum delivery barrier, and thus, maximum penetration of the drug is necessary. While in place, the stratum corneum delays penetration to the target tissue and sustains the time that the dissolved active drug resides in the target tissue. During this stage of the lesion, microparticulate drug will not significantly cross the intact stratum corneum, and thus, has no real effect in treatment of the lesion. Once the herpes lesion vesicles rupture, the stratum corneum is no longer in place, and the dissolved drug rapidly sweeps past the target tissue, providing minimal or insignificant benefit. However, from the time that the vesicle ruptures and through to the complete formation of the scab, the microparticulate drug is deposited directly at the target area, where it can slowly be released for sustained and significant therapeutic benefit. Thus, in order to adequately dose the viable epidermis from the prodrome through the time of scab formation in a herpes lesion, two distinctly different drug delivery strategies must be implemented.

While the dermatological conditions of acne and herpes lesions serve as conceptual examples of how therapeutic approaches can require dramatically different drug delivery profiles, all skin diseases are best treated by a particular drug delivery strategy tailored specifically to the pharmaceutical and the particular disease. Some diseases are best treated using pulsed or spiked delivery in which high levels of drug are delivered in a short period of time. This type of treatment saturates receptor sites and provides maximum microbial or viral replication inhibition, thus providing optimal therapy for certain diseases. Conversely, a cosmetic, topical, or transdermal product that provides steady state active pharmaceutical delivery while minimizing excipient delivery provides the preferred skin delivery profile for other diseases. Thus, a carrier system that is can be adjusted to optimize the delivery profile for the pharmacology of the active drug and the nature of the disease state is needed to advance the effectiveness of pharmaceutical products applied to the skin.

SUMMARY OF THE INVENTION

The present invention concerns a pharmaceutical carrier system comprising a dermatological composition that is a semi-solid aqueous gel, wherein a pharmaceutical is dissolved in the gel such that the pharmaceutical has the capacity to cross the stratum corneum layer of the epidermis and become available systemically, and wherein the composition also contains pharmaceutical in a microparticulate state that does not readily cross the stratum corneum of the epidermis. The ratio of microparticulate pharmaceutical to dissolved pharmaceutical is adjustable, but is preferably five or less. The microparticulate pharmaceutical and the dissolved pharmaceutical may be the same drug, or they may be different drugs.

Methods for preparing the compositions of the present invention are also shown. In addition, methods for treating dermatological conditions that include topically applying the dermatological compositions of the invention are shown. More particularly, the invention concerns methods for treating dermatological conditions or diseases such as acne, herpes lesions, and dermatitis. Antimicrobial agents having anti-inflammatory properties such as dapsone are used to treat acne. Antiviral agents or antiviral agents in combination with local anesthetics are used to treat herpes lesions, and anti-inflammatory agents are used to treat dermatitis.

DESCRIPTION OF THE PREFERRED EMBODIMENTS

The present invention comprises compositions for application to the skin that can form microparticulate drug precipitates in adjustable ratios of microparticulate drug to dissolved drug, methods for the formation of said compositions, and methods for treatment of skin conditions using said compositions. The advantages of the present invention are appreciated in the treatment of skin conditions or diseases by using cosmetics or topical pharmaceuticals, and in the systemic treatment of illness by using transdermal pharmaceuticals. The present invention is particularly effective in the treatment of acne with antimicrobial actives known to possess anti-inflammatory properties such as dapsone. The invention also finds particular use in the treatment of herpes lesions and dermatitis.

In one embodiment, the present invention is directed to a novel pharmaceutical carrier system comprising a dermatological composition that is a semisolid aqueous gel, wherein the composition exhibits an optimal balance between a dissolved pharmaceutical that is available to cross through the stratum corneum to become systemically available, and a microparticulate pharmaceutical that is retained in or above the stratum corneum to serve as a reservoir or to provide drug action in the supracorneum zone. The microparticulate pharmaceutical and the dissolved pharmaceutical may be the same or different drugs. The microparticulate pharmaceutical may comprise a crystalline precipitant or an amorphous precipitant.

Optimal balance is accomplished by having a semisolid gel carrier system in which microparticulate pharmaceutical precipitates are formed in reproducible ratios with respect to the dissolved pharmaceutical. For the composition to have a wide range of applicability, the microparticulate to dissolved pharmaceutical ratio preferably should be no greater than five, at therapeutic levels of applied active pharmaceutical.

A composition having a microparticulate to dissolved pharmaceutical ratio of less than two may provide the greatest amount of pharmaceutical available for immediate partition out of the stratum corneum and into the viable epidermis. This should provide minimum reservoir capacity, but may not maintain sustained delivery or provide maximum activity in the supracorneum zone. A composition having a microparticulate to dissolved pharmaceutical ratio of two or greater may have a reduced amount of drug available for immediate partition out of the stratum corneum and into the viable epidermis. This provides maximum reservoir capacity, and maintains sustained delivery, providing maximum activity in the supracorneum zone. For the present invention, the ratio for microparticulate drug to dissolved drug should be no greater than 50, preferably no greater than 10, and most preferably no greater than 5. Drug delivery from the microparticulate/dissolved pharmaceutical formulation may be optimized to provide higher levels of drug to the supracorneum zone, while maintaining the level of drug partitioning out of the stratum corneum and into the viable epidermis, despite 10-fold increases in the amount of pharmaceutical applied to the skin.

The compositions of the present invention comprise semisolid and gel-like vehicles that include a polymer thickener, water, preservatives, active surfactants or emulsifiers, antioxidants, sunscreens, and a solvent or mixed solvent system. The solvent or mixed solvent system is important to the formation of the microparticulate to dissolved pharmaceutical ratio. The formation of the microparticulate, however, should not interfere with the ability of the polymer thickener or preservative systems to perform their functions.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably, the gelling agent comprises between about 0.2% to about 4% by weight of the composition. More particularly, the preferred compositional weight percent range for "CARBOPOL®" is between about 0.5% to about 2%, while the preferred weight percent range for "NATROSOL®)" and "KLUCEL®" is between about 0.5% to about 4%. The preferred compositional weight percent range for both "HYPAN®" and "STABILEZE®" is between about 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sunscreens include methyl cinnamate. Moreover, BHA may be used as an antioxidant, as well as to protect ethoxydiglycol and/or dapsone from discoloration due to oxidation. An alternate antioxidant is BHT.

Pharmaceuticals for use in all embodiments of the invention include antimicrobial agents, anti-inflammatory agents, antiviral agents, local anesthetic agents, corticosteroids, destructive therapy agents, antifungals, and antiandrogens. In the treatment of acne, active pharmaceuticals that may be used include antimicrobial agents, especially those having anti-inflammatory properties such as dapsone, erythromycin, minocycline, tetracycline, clindamycin, and other antimicrobials. The preferred weight percentages for the antimicrobials are 0.5% to 10%. In the topical treatment of herpes lesions, active pharmaceuticals that may be used include antiviral or local anesthetic agents. A concentration of about 1.0% to 10% by weight is preferred for nucleoside analogues such as acyclovir, famciclovir, penciclovir, valacyclovir, and ganciclovir.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. A preferred concentration for local anesthetics is about 0.025% to 5% by weight of the total composition. Anesthetics such as benzocaine may also be used at a preferred concentration of about 2% to 25% by weight.

Corticosteroids that may be used include betamethasone dipropionate, fluocinolone acetonide, betamethasone valerate, triamcinolone acetonide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. Preferred concentrations for corticosteroids such as hydrocortisone or methylprednisolone acetate are from about 0.2% to about 5.0% by weight.

Destructive therapy agents such as salicylic acid or lactic acid may also be used. A concentration of about 2% to about 40% by weight is preferred. Cantharidin is preferably utilized in a concentration of about 5% to about 30% by weight. Typical antifungals that may be used in this invention and their preferred weight concentrations include: oxiconazole nitrate (0.1% to 5.0%), ciclopirox olainine (0.1% to 5.0%), ketoconazole (0.1% to 5.0%), miconazole nitrate (0.1% to 5.0%), and butoconazole nitrate (0.1% to 5.0%). For the topical treatment of seborrheic dermatitis, hirsutism, acne, and alopecia, the active pharmaceutical may include an antiandrogen such as flutamide or finasteride in preferred weight percentages of about 0.5% to 10%.

Typically, treatments using a combination of drugs include antibiotics in combination with local anesthetics such as polymycin B sulfate and neomycin sulfate in combination with tetracaine for topical antibiotic gels to provide prophylaxis against infection and relief of pain. Another example is the use of minoxidil in combination with a corticosteroid such as betamethasone diproprionate for the treatment of alopecia ereata. The combination of an anti-inflammatory such as cortisone with an antifungal such as ketoconazole for the treatment of tinea infections is also an example.

In one embodiment, the invention comprises a dermatological composition having about 0.5% to 4.0% carbomer and about 0.5% to 10% of a pharmaceutical that exists in both a dissolved state and a microparticulate state. The dissolved pharmaceutical has the capacity to cross the stratum corneum, whereas the microparticulate pharmaceutical does not. Addition of an amine base, potassium hydroxide solution, or sodium hydroxide solution completes the formation of the gel. More particularly, the pharmaceutical may include dapsone, an antimicrobial agent having anti-inflammatory properties. A preferred ratio of microparticulate to dissolved dapsone is five or less.

In another embodiment, the invention comprises about 1% carbomer, about 80–90% water, about 10% ethoxydiglycol, about 0.2% methylparaben, about 0.3% to 3.0% dapsone including both microparticulate dapsone and dissolved dapsone, and about 2% caustic material. More particularly, the carbomer may include "CARBOPOL®980" and the caustic material may include sodium hydroxide solution.

In a preferred embodiment, the composition comprises dapsone and ethoxydiglycol, which allows for an optimized ratio of microparticulate drug to dissolved drug. This ratio determines the amount of drug delivered, compared to the amount of drug retained in or above the stratum corneum to function in the supracorneum domain. The system of dapsone and ethoxydiglycol may include purified water combined with "CARBOPOL®" gelling polymer, methylparaben, propylparaben, titanium dioxide, BHA, and a caustic material to neutralize the "CARBOPOL®."

Another preferred embodiment of this invention relates to a composition for the treatment of herpes lesions comprising a semisolid aqueous gel; a first pharmaceutical in the gel, partially in a microparticulate form and partially in a dissolved form, where optimized delivery for early state lesions is provided when the pharmaceutical is dissolved and optimized delivery for later state lesions is provided when the pharmaceutical is in a microparticulate form; and a second pharmaceutical dissolved in the gel which provides benefit throughout lesion progression. In a preferred embodiment, the composition comprises acyclovir and 1-methyl-2-pyrrolidone, which allows for an optimized ratio of microparticulate drug to dissolved drug for the treatment of herpes lesions. Acyclovir may be present in dissolved and microparticulate forms. The ratio determines the amount of drug delivered up to the point of lesion vesicle formation, as compared to the amount of drug available to be deposited into the lesion once the vesicles rupture. The drug delivery system of acyclovir and 1-methyl-2-pyrrolidone may include purified water combined with KLUCEL® hydroxypropyl cellulose gelling polymer, methylparaben, and propylparaben.

In another preferred embodiment, a combination drug system of acyclovir and tetracaine HCl may be formulated with 1-methyl-2-pyrrolidone to provide both antiviral and local anesthetic activity. Tetracaine HC1 is a local anesthetic that alters membrane function and blocks pain. In a preferred embodiment, acyclovir comprises 5% by weight of the composition. The system of acyclovir, tetracaine HC 1, and 1-methyl-2-pyrrolidone can include purified water, sodium lauryl sulfate, KLUCEL® hydroxypropyl cellulose gelling polymer, methylparaben, and propylparaben. The combination of a local anesthetic with sodium lauryl sulfate has been shown to be an effective therapy for herpes lesions. The combination of the nucleoside analogue acyclovir with the anesthetic/late stage antiviral combination tetracaine HCl and sodium lauryl sulfate should provide complete topical therapy for herpes lesions.

The relative percentages for each of the reagents used in the present invention may vary depending upon the desired strength of the target formulation, gel viscosity, and the desired ratio of microparticulate to dissolved pharmaceutical. Unless otherwise designated, all reagents listed above are commonly known by one of ordinary skill in the art and are commercially available from pharmaceutical or cosmetic excipient suppliers.

The present invention also provides methods for preparing the dermatological compositions described above. In a general form, the method for producing a dermatological gel composition having dissolved drug and microparticulate drug precipitates comprises the steps of completely dissolving a pharmaceutical in a solvent or solvent mixture; adding and adequately dispersing a polymeric thickener in water; and combining the dissolved pharmaceutical with the dispersed polymeric thickener. Alternatively, water may be slowly added to the dissolved pharmaceutical, followed by the addition of a polymeric thickener. Ethoxydigylcol and 1-methyl-2-pyrollidone are preferred solvents for use in this invention.

In one preferred embodiment, the method for preparing a dermatological composition having dissolved and microparticulate pharmaceutical comprises the steps of forming a homogenous dispersion by stirring purified water vigorously enough to form a vortex and sifting gel polymer into the vortex formed in the water while continuing to stir; forming a pharmaceutical component by dissolving methyl paraben and propylparaben in ethoxydiglycol by mixing to form a solution, and mixing an active pharmaceutical with the solution until the pharmaceutical dissolved; mixing the pharmaceutical component with the homogenous dispersion to form a microparticulate pharmaceutical dispersion; and adding a caustic material. The active pharmaceutical may comprise any of the types mentioned above. In a preferred embodiment, the active pharmaceutical comprises dapsone. In another preferred embodiment, the active pharmaceutical comprises acyclovir or acyclovir in combination with tetracaine or tetracaine HCl.

The order in which reagents are combined may be important, depending on the particular reagents necessary for the target mixture. For example, after a pharmaceutical such as dapsone is dissolved in a solvent such as ethoxydiglycol, water may be slowly added to the dapsone in the ethoxydiglycol solution, or the dapsone in ethoxydiglycol solution may be added to the water with mixing. Adding the dapsone in ethoxydiglycol solution to water may result in less polydispersity in the size of the microparticulates than adding water to the dapsone in ethoxydiglycol solutions.

The carbomer is generally dispersed in the water component of the formulation, while the remaining ingredients will be dissolved or dispersed in whichever of the two components are best for dissolving or dispersing the ingredient. For example, it is suggested to dissolve methylparaben, propylparaben, and BHA in ethoxydiglycol. After the ethoxydiglycol component and water component are combined, neutralizer is added to formulate the gel.

Finally, in another embodiment of the invention, methods for the treatment of dermatological conditions by topical application of the compositions of this invention are shown. These methods are useful in the treatment of diseases such as acne, herpes lesions, seborrhea dermatitis, hirsutism, and alopecia. In a preferred embodiment, a method for the treatment of dermatological conditions comprises applying topically a gel composition comprising a dissolved pharmaceutical that has the capacity to cross the stratum corneum of the epidermis and become systemically available, and a microparticulate pharmaceutical that has only minimal capacity to cross the stratum corneum in its microparticulate state. In one embodiment, the dissolved pharmaceutical and microparticulate pharmaceutical comprise about 1.0% to 10% antiviral agent. In another embodiment, the dissolved pharmaceutical and microparticulate pharmaceutical comprise about 0.5% to 10% antiandrogen.

In a preferred embodiment, a method for the treatment of acne comprises applying topically a gel composition that comprises a dissolved anti-inflammatory pharmaceutical and a microparticulate antimicrobial pharmaceutical, wherein the dissolved anti-inflammatory pharmaceutical crosses the stratum corneum of the epidermis and is absorbed into the lower two-thirds of the pilosebaceous unit, while the microparticulate antimicrobial pharmaceutical is primarily delivered into the upper third of the pilosebaceous unit, crossing the stratum corneum of the epidermis only minimally. Preferably, the dissolved pharmaceutical and microparticulate pharmaceutical comprise dapsone.

In another preferred embodiment, a method for the treatment of herpes lesions comprises applying topically a semisolid gel composition that comprises a semisolid aqueous gel; a first pharmaceutical in the gel, which exists in a partially microparticulate form and a partially dissolved form, providing for optimized delivery for early state lesions when dissolved and optimized delivery for later state lesions when present as a microparticulate; and a second pharmaceutical dissolved in the gel, providing benefit throughout progression of the lesion. Preferably, the first pharmaceutical comprises a nucleoside analogue, and the second pharmaceutical comprises a local anesthetic. In a preferred embodiment, the nucleoside analogue comprises acyclovir, penciclovir, famciclovir, valacyclovir, or ganciclovir, and the local anesthetic comprises tetracaine, dyclonine, dibucaine, or a salt thereof, such as tetracaine HCl, dyclonine HCl, or dibucaine HCl. More preferably, acyclovir comprises 5% by weight of the composition, and tetracaine HCl comprises 2–5% by weight.

The following examples are provided to enable those of ordinary skill in the art to make and use the methods and compositions of the invention. These examples are not intended to limit the scope of what the inventors regard as their invention. Additional advantages and modifications will be readily apparent to those skilled in the art.

Examples 1 through 6 describe methods for the preparation of compositions of the invention that include microparticulate crystalline dapsone, dissolved dapsone, and combinations of the two. The examples offer illustrations of methods that can be used to control the ratio of dissolved to microparticulate pharmaceuticals in the final product. Since microparticulate pharmaceuticals are retained above the stratum corneum having negligible penetration and dissolved pharmaceuticals penetrate the stratum corneum, controlling the ratios between the two epidermal areas is important in developing a composition having an optimal delivery route for administering pharmaceuticals via the skin.

Example 7 describes a method for the preparation of compositions of this invention using two different pharmaceuticals in combination, resulting in one pharmaceutical dissolved in the composition and the other present in a microparticulate state, such that two epidermal areas may be treated with two different drugs. Example 8 provides a method for preparing a composition having a pharmaceutical partially in a microparticulate state and partially dissolved, combined with a different dissolved pharmaceutical. Examples 9–11 provide evaluations of the compositions and methods described herein.

EXAMPLE 1

The following example provides a method for producing a topical therapeutic agent in which the pharmaceutical component is a combination of dissolved and microcrystalline dapsone. Because of the nature of the microcrystalline dapsone in the final product of Example 1, microcrystalline dapsone will be retained in or above the stratum corneum and will therefore serve as a reservoir or provide drug action in the supracorneum zone. The dissolved dapsone will pass through the stratum corneum. The method of Example 1 can also be used to produce a composition of this invention that includes other pharmaceuticals such as those described above.

A polymer thickener component was prepared by charging 85.7 grams of purified water to a vessel suitable to contain 100 grams of finished semisolid product, and slowly sifting one gram of "CARBOPOL® 980" into a vortex formed by rapidly stirring the purified water. When a homogeneous dispersion of "CARBOPOL® 980" and water was formed, stirring was reduced to minimize air entrapment. Next, an active pharmaceutical component was prepared by charging an appropriately sized container with 10.0 g of ethoxydiglycol. 0.2 g of methylparaben and 0.1 g of propylparaben were added to the ethoxydiglycol and mixed until all of the crystalline solid was dissolved. 1.0 g dapsone was added to the ethoxydiglycol and mixed until the drug was completely dissolved.

The polymer thickener component was added to the pharmaceutical component with mixing, and immediately resulted in the formation of crystalline microparticles. Once the dispersion was homogenous, 2.0 grams of a 10% w/w aqueous sodium hydroxide solution were added to neutralize the CARBOPOL® 980 and form the gel.

EXAMPLE 2

The following example provides another topical therapeutic agent in which the pharmaceutical component is dissolved dapsone. The method of Example 2 can also be used to produce a composition of this invention that includes other pharmaceuticals.

To prepare the composition of Example 2, the procedure of Example 1 was followed using the following specific weights of reagents. All dapsone was dissolved in the final product gel, and thus, crystalline microparticles did not form when the polymer thickener component was added to the pharmaceutical component. All reagent weights are shown per 100 grams of product.

| Component | wt/100 g product |
|---|---|
| Polymer Thickener Component | |
| Water | 86.67 g |
| "CARBOPOL 980" | 1.0 g |
| Active Pharmaceutical Component | |
| Ethoxydiglycol | 10.0 g |
| Methylparaben | 0.2 g |
| Propylparaben | 0.1 g |
| Dapsone | 0.03 g |
| Caustic/Amine Component | |
| 10% w/w Sodium Hydroxide | 2.0 g |

EXAMPLE 3

The following example provides yet another topical therapeutic agent in which the pharmaceutical component is dissolved dapsone. The method of Example 3 can also be used to produce a composition of this invention that includes other pharmaceuticals such as those designated in this application.

The procedure of Example 1 was followed using reagents in the amounts designated below. All of the dapsone was dissolved in the final product gel, thus crystalline microparticles did not form upon adding the polymer thickener component to the pharmaceutical component. All reagent weights are shown per 100 grams of product.

| Component | wt/100 g product |
|---|---|
| Polymer Thickener Component | |
| Water | 86.6 g |
| "CARBOPOL 980" | 1.0 g |
| Active Pharmaceutical Component | |
| Ethoxydiglycol | 10.0 g |
| Methylparaben | 0.2 g |
| Propylparaben | 0.1 g |
| Dapsone | 0.1 g |
| Caustic/Amine Component | |
| 10% w/w Sodium Hydroxide | 2.0 g |

EXAMPLE 4

The following example provides yet another topical therapeutic agent in which the pharmaceutical component is dissolved dapsone. The method of Example 4 can also be used to produce a composition of this invention that includes other pharmaceuticals such as those designated in this application.

The procedure of Example 1 was followed using reagents in the amounts designated below. All reagent weights are shown per 100 grams of product.

| Component | wt/100 g product |
|---|---|
| Polymer Thickener Component | |
| Water | 86.4 g |
| "CARBOPOL 980" | 1.0 g |
| Active Pharmaceutical | |
| Ethoxydiglycol | 10.0 g |
| Methylparaben | 0.2 g |
| Propylparaben | 0.1 g |
| Dapsone | 0.3 g |
| Caustic/Amine Component | |
| 10% w/w Sodium Hydroxide | 2.0 g |

EXAMPLE 5

The following example provides yet another topical therapeutic agent in which the pharmaceutical component is a combination of dissolved and microcrystalline dapsone. Because of the nature of the microcrystalline dapsone in the final product of Example 5, it will be primarily retained in or above the stratum corneum and will therefore serve as a reservoir or provide drug action in the supracorneum zone. The method of Example 5 can also be used to produce a composition of this invention that includes other pharmaceuticals such as those designated in this application.

The procedure of Example 1 was followed using reagents in the amounts designated below. All reagent weights are shown per 100 grams of product.

| Component | wt/100 g product |
|---|---|
| Polymer Thickener Component | |
| Water | 86.2 g |
| "CARBOPOL 980" | 1.0 g |
| Active Pharmaceutical Component | |
| Ethoxydiglycol | 10.0 g |
| Methylparaben | 0.2 g |
| Propylparaben | 0.1 g |
| Dapsone | 0.5 g |
| Caustic/Amine Component | |
| 10% w/w Sodium Hydroxide | 2.0 g |

EXAMPLE 6

The following example provides a method for producing a topical therapeutic agent in which the pharmaceutical component is a combination of dissolved and microcrystalline dapsone. Because of the nature of the microcrystalline dapsone in the final product of Example 6, it will be retained in or above the stratum corneum and will therefore serve as a reservoir or provide drug action in the supracorneum zone. The method of Example 6 can also be used to produce a composition of this invention that includes other pharmaceuticals such as those designated in this application.

The procedure of Example 1 was followed using reagents in the amounts designated below. All reagent weights are shown per 100 grams of product.

| Component | wt/100 g product |
|---|---|
| Polymer Thickener Component | |
| Water | 83.7 g |
| "CARBOPOL 980" | 1.0 g |
| Active Pharmaceutical Component | |
| Ethoxydiglycol | 10.0 g |
| Methylparaben | 0.2 g |
| Propylparaben | 0.1 g |
| Dapsone | 3.0 g |
| Caustic/Amine Component | |
| 10% w/w Sodium Hydroxide | 2.0 g |

EXAMPLE 7

Example 7 describes a method for preparing a composition of this invention that includes a microparticulate crystalline pharmaceutical, dapsone, in combination with a different dissolved pharmaceutical, dyclonine HCl. Since microparticulate pharmaceuticals are retained above the stratum corneum having negligible penetration and dissolved pharmaceuticals penetrate the stratum corneum, using different drugs for the two forms (microparticulate and dissolved) enables treating the two epidermal areas with different drugs. This allows further options to develop optimal delivery routes for administering pharmaceuticals via the skin.

An active pharmaceutical component was prepared by charging an appropriately sized container with 15.0 g of ethoxydiglycol. 0.3 g methylparaben and 0.15 g of propylparaben were added to the ethoxydiglycol and mixed until all of the crystalline solid was dissolved. 1.5 g of dapsone were added to the ethoxydiglycol and mixed until the drug was completely dissolved.

An active pharmaceutical component which would remain dissolved was prepared by charging an appropriately sized container with 127.8 grams of purified water. 1.5 grams of dyclonine HCl was added to the water with mixing until all of the drug was completely dissolved.

The solvent phase was added to the aqueous phase and crystalline microparticles of dapsone were immediately formed. 3.75 grams of "NATROSOL®" 250 PHARM were added to form a topical gel containing microcrystalline dapsone and dissolved dyclonine HCl. The presence of microcrystalline dapsone was confirmed by optical microscopy.

EXAMPLE 8

Example 8 describes a method for preparing a composition of this invention that includes a pharmaceutical partially in a microparticulate form and partially in a dissolved form in combination with a different dissolved pharmaceutical. The composition finds particular use in the treatment of herpes lesions. The pharmaceutical in both dissolved and microparticulate forms provides optimized delivery for early stage lesions when dissolved and optimized delivery for later stage lesions when present as a microparticulate. The other dissolved pharmaceutical provides benefit throughout the lesion progression.

An active pharmaceutical component was prepared by charging an appropriately sized container with 44.0 g of 1-methyl-2-pyrrolidone. 0.16 g methylparaben and 0.08 g propylparaben as preservatives were added to the 1-methyl-2-pyrrolidone and mixed until all the crystalline solid dissolved. 8.0 g 1 N NaOH was mixed with the 1-methyl-2-pyrrolidone and preservative mixture prior to the addition of 4.0 g acyclovir. Upon heating to approximately 50° C., all of the added materials dissolved to form a single phase clear solution.

An active pharmaceutical component which would remain dissolved was prepared by charging an appropriately sized container with 17.36 g purified water. 4.0 g tetracaine HCl and 0.8 g of sodium lauryl sulfate was added to the water with mixing until all of the solids were dissolved.

The solvent phase was added to the aqueous phase and crystalline microparticles of acyclovir were immediately formed. 1.60 grams of KLUCEL® HF hydroxypropyl cellulose were added to form a topical gel containing microcrystalline acyclovir, dissolved acyclovir, and dissolved tetracaine HCl and sodium lauryl sulfate. The presence of microcrystalline acyclovir was confirmed by optical microscopy.

EXAMPLE 9

Evaluation

Example 9 evaluates the compositions of examples 1–6 and demonstrates that increasing the dapsone content of this invention's composition from 0 to 0.3% increases the amount of dapsone that permeates into the skin, whereas further increasing dapsone above 0.3% results in microparticulate dapsone that remains above the stratum corneum or supracorneum zone. Therefore, the amount of dapsone that permeates into the skin does not increase incrementally for compositions having increased dapsone above 0.3%.

In example 9, experiments were performed by loading excised human skin on a standard Franz type vertical diffusion cell having a 15 mm orifice, 7.0 ml volume, and equipped with a Hanson Helix stirrer using a phosphate buffered saline/ethoxydiglycol mixture as the receptor phase. The full thickness of human abdominal skin was removed from a cadaver within 24 hours of death. The subcutaneous tissue was removed using a #22 scalpel blade. The tissue was cut into 5×15 cm sections with care being taken to avoid contamination of the stratum corneum with subcutaneous fat. Each 5×15 cm section was placed in a sterile plastic bag and stored on wet ice until being placed in the freezer (maximum transport time 2 hours). A single 5×15 cm section of skin was removed from the freezer on the day of an in-vitro skin permeation study. The skin was thawed, rinsed, patted dry with a tissue, and loaded on the Franz diffusion cell. Samples were dosed with 10 mg of the formulation i.e. finite dosing. Receptor solutions were assayed by reverse phase HPLC using UV detection.

The cumulative drug concentration in the receptor solution was monitored over a 72 hour period. The data in Table 1 shows the mean quantities of drug transported for quadruplicate in-vitro skin permeation experiments in which each formulation was evaluated using the same donor skin on each of four different days. As seen in Table 1, the cumulative amount of dissolved dapsone that was transported across the stratum corneum increased until the dapsone level at which the formation of microparticulate dapsone was reached, i.e. up to 0.3 weight percent dapsone. At concentrations above 0.3%, the amount of dissolved drug did not increase, and the amount of drug delivered remained the same. Thus, the excess drug (above 0.3 weight percent) was retained in the stratum corneum or supracorneum zone.

For this drug delivery system, the microparticulate to dissolved pharmaceutical ratio of 1.5 to 15 resulted in increasing amounts of drug available for antimicrobial action in the supracorneum zone, while maintaining a set amount of dapsone available for anti-inflammatory activity in the viable epidermis.

TABLE 1

Dapsone Concentration in Receptor Solution Following in-vitro Dosing of 10 mg of Topically Applied Semisolid

| Dapsone Semisolid Concentration (% w/w) | Example Number | µg Dapsone/ 1.77 cm² by 72 hrs | % of Applied Dose transported by 72 hrs |
|---|---|---|---|
| 0.03 | 2 | 0.35 ± 0.1 | 11 |
| 0.1 | 3 | 0.73 ± 0.3 | 7 |
| 0.3 | 4 | 2.6 ± 2.2 | 8 |
| 0.5 | 5 | 2.2 ± 0.8 | 4 |
| 1.0 | 1 | 2.9 ± 1.7 | 3 |
| 3.0 | 6 | 3.3 ± 2.5 | 1 |

EXAMPLE 10

Evaluation

Example 10 demonstrates the importance of using the optimum microparticulate to dissolved pharmaceutical ratio. The results in Table 2 show that for the same amount of applied drug, the amount of drug in the supracorneum zone can be optimized by improving the microparticulate to dissolved pharmaceutical ratio.

In example 10, the procedures of example 9 were used, including Franz diffusion cell and experimental technique, however 1% dapsone formulations were compared. Formulation number 1 was manufactured according to example 1 and contained 1% dapsone and 10% ethoxydiglycol having a microparticulate drug/dissolved drug ratio of 5. Formulation number 2 had the composition 1% dapsone, 25% ethoxydiglycol, 70.7% water, 1% "CARBOPOL 980," 0.2% methylparaben, 0.1% propylparaben, and 2% sodium hydroxide solution (10% w/w). For formulation number 2, all of the dapsone is dissolved with no microparticulate drug present.

Approximately 10 mg of product was rubbed into the skin, and after 72 hours, the skin surface was tape stripped to remove all supracorneum drug. The skin was cut into small pieces and extracted while the receptor solution was directly assayed. For formulation number 1 (microparticulate to dissolved drug ratio equal to 5) 68±4% of the applied dose remained in the supracorneum zone, while only 52±3% of formulation 2 (particulate to dissolved drug ratio=0) remained in the supracorneum zone. Each value is the mean of triplicate experiments.

TABLE 2

Distribution of Dapsone in Different Skin Layers by 72 hrs of in-vitro Permeation Study

| Formulation | 1% DDS Hydrogel in 10% DGME (microcrystal form) | 1% DDS Hydrogel in 25% DGME (soluble form) |
|---|---|---|
| Receptor | 0.92% ± 0.14 | 1.29% ± 0.24 |
| Surface residual | 68.42% ± 3.84 | 52.51% ± 2.88 |
| Stratum corneum | 15.54% ± 4.12 | 32.15% ± 6.16 |
| Dermal | 13.59% ± 2.15 | 14.06% ± 7.31 |
| Total recovery | 60.7% ± 5.3 | 53.7% ± 7.7 |

EXAMPLE 11

Evaluation

Example 11 demonstrates that a 2% acyclovir solution in 1-methyl-2 pyrrolidone provides the same level of intact skin delivery as a 5% acyclovir gel formulation that contains approximately 2% dissolved acyclovir and 3% microparticulate acyclovir. These delivery results are compared with the Spruance (1986 Antimicrobial Agents and Chemotherapy, Vol. 29, No. 5, Pgs. 730–732) standard acyclovir intact skin delivery formulation comprised of 5% acyclovir dissolved in 95% dimethyl sulfoxide (DMSO). The 95/5 DMSO/acyclovir standard formulation is known to be 60-fold more permeable than the commercially available ZOVIRAX® Ointment (5% acyclovir in a polyethylene glycol base).

In example 11, the procedures of example 9 were used except that 50–500 microliter doses of formulations were applied to dermatomed human skin which was not frozen until after 48 hours post-mortem. The formulation of example 8 which contains 5% acyclovir (of which approximately 40% is dissolved and 60% is in a microparticulate form) was tested along with a 2% acyclovir in 1-methyl-2-pyrrolidone. In direct comparison with the 95/5 DMSO/acyclovir skin delivery standard, both the 5% acyclovir combination gel of example 8 and the 2% acyclovir in 1-methyl-2-pyrrolidone solution delivered 20–25% of the acyclovir delivery standard. The presence of crystalline microparticulate drug does not increase the delivery of acyclovir across intact skin. The delivery of the dissolved acyclovir is considered optimized since it was more than 1 0-fold greater than skin delivery of acyclovir from the commercialized ZOVIRAX® formulation.

Those skilled in the art will recognize that, while specific embodiments have been illustrated and described, various modifications and changes may be made without departing from the spirit and scope of the invention.

What is claimed is:

1. A dermatological composition comprising:
   a semisolid aqueous gel;
   a pharmaceutical dissolved in said gel, wherein said dissolved pharmaceutical crosses the stratum corneum layer of the epidermis and becomes available systemically; and
   a microparticulate pharmaceutical dispersed in said gel, wherein said microparticulate pharmaceutical does not cross the stratum corneum of the epidermis in its microparticulate state, and wherein the ratio of said microparticulate to dissolved pharmaceutical is at least 5:1.

2. The composition of claim 1, wherein said gel comprises carbomer, hydroxyethylcellulose, hydroxypropylcellulose, cellulose gum, methylvinyl ether/maleic anhydride (MVE/MA) decadiene crosspolymer, or polyvinylmethyl ether/maleic acid (PVM/MA) copolymer.

3. The composition of claim 1, wherein said gel comprises a cross-linked acrylic acid polymer dissolved in an aqueous phase and a caustic material.

4. The composition of claim 1, wherein said microparticulate pharmaceutical is a crystalline precipitant.

5. The composition of claim 1, wherein said microparticulate pharmaceutical is an amorphous precipitant.

6. The composition of claim 1, wherein said dissolved pharmaceutical and microparticulate pharmaceutical comprise an antimicrobial agent, anti-inflammatory agent, antiviral agent, local anesthetic, corticosteroid, destructive therapy agent, antifungal agent, or antiandrogen agent.

7. The composition of claim 1, wherein said microparticulate pharmaceutical and dissolved pharmaceutical comprise different pharmaceuticals.

8. A dermatological composition, comprising a semisolid aqueous gel having about 0.5% to 4.0% carbomer; about 0.5% to 10% pharmaceutical, wherein said pharmaceutical comprises a dissolved pharmaceutical having the capacity to cross the stratum corneum of the epidermis and become systemically available and a microparticulate pharmaceutical that does not cross the stratum corneum of the epidermis in its microparticulate state; and an amine base, sodium hydroxide solution, or potassium hydroxide solution, and wherein the ratio of said microparticulate to dissolved pharmaceutical is at least 5:1.

9. The dermatological composition of claim 8, wherein said dissolved pharmaceutical and said microparticulate pharmaceutical comprise dapsone.

10. The composition of claim 8 wherein said pharmaceutical comprises an antimicrobial agent, antiviral agent, anti-inflammatory agent, local anesthetic, corticosteroid, destructive therapy agent, antifungal agent, or antiandrogen agent.

11. A dermatological gel composition for the treatment of herpes lesions comprising:
    a semisolid aqueous gel;
    a first pharmaceutical in said gel, partially in a microparticulate form and partially in a dissolved form, wherein said first pharmaceutical provides optimized delivery for early state lesions when dissolved and optimized delivery for later state lesions when present as a microparticulate; and wherein the ratio of said microparticulate to dissolved first pharmaceutical is at least 5:1 and
    a second pharmaceutical dissolved in said gel, wherein said second pharmaceutical provides benefit throughout lesion progression.

12. The composition of claim 11, wherein said first pharmaceutical comprises a nucleoside analogue selected from the group consisting of acyclovir, penciclovir, famciclovir, valacyclovir, and ganciclovir, and said second pharmaceutical comprises a local anesthetic selected from the group consisting of tetracaine, tetracaine HCl, dyclonine, dyclonine HCl, dibucaine, and dibucaine HCl.

13. The composition of claim 12, wherein said acyclovir comprises 5% by weight of the composition.

14. The composition of claim 12, wherein said tetracaine HCl comprises 5% by weight of the composition.

15. A dermatological composition, comprising a semisolid aqueous gel having about 0.5% to 4.0% carbomer; about 0.5% to 10% dapsone, wherein said dapsone is dissolved and has the capacity to cross the stratum corneum of the epidermis an become systemically available and a microparticulate pharmaceutical lacking the ability to cross the stratum corneum of the epidermis in its microparticulate state; and an amine base, sodium hydroxide solution, or potassium hydroxide solution.

* * * * *